US00PP15287P3

(12) United States Plant Patent
Warner

(10) Patent No.: US PP15,287 P2
(45) Date of Patent: Nov. 2, 2004

(54) SHRUB ROSE PLANT NAMED 'CHEWPEACHDELL'

(50) Latin Name: *Rosa hybrida*
Varietal Denomination: CHEwpeachdell

(75) Inventor: Christopher H. Warner, Newport Shropshire (GB)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 10/306,924

(22) Filed: Nov. 29, 2002

(65) Prior Publication Data

US 2004/0107466 P1 Jun. 3, 2004

(51) Int. Cl.[7] ..... A01H 5/00
(52) U.S. Cl. ..... Plt./102
(58) Field of Search ..... Plt./102

*Primary Examiner*—Anne Marie Grunberg
*Assistant Examiner*—Annette H Para
(74) *Attorney, Agent, or Firm*—Christie, Parker & Hale, LLP

(57) ABSTRACT

A new variety of Shrub rose suitable for garden decoration, having flowers of peach coloration.

1 Drawing Sheet

Classification: The present invention relates to a new *Rosa hybrida* plant.

Variety denomination: The new plant has the varietal denomination 'CHEwpeachdell'.

BACKGROUND OF THE INVENTION

This invention relates to a new and distinct variety of Shrub Rose. The varietal denomination of the new variety is 'CHEwpeachdell'. It has as its seed parent the variety known as 'CHEwarvel' (U.S. Plant Pat. No. 9,012) and as its pollen parent the variety known as 'DICmagic' (not patented).

SUMMARY OF THE INVENTION

Among the features which distinguish the new variety from other presently available and commercial rose cultivars known to the inventor are the following combination of characteristics: its very upright to nearly columnar habit, its numerous petaloids in the flower, its nearly flat upper side of the rachis, its red pigmentation on the rachis and the stipule of the young leaf and its lack of extension in bud length from before the calyx breaks to after the calyx breaks. The plant has a very upright to nearly columnar growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'CHEwpeachdell' may be asexually propagated by cuttings, budding and grafting.

COMPARISON WITH PARENTS

The new rose may be distinguished from its seed parent, 'CHEwarvel' by the following combination of characteristics: 'CHEwpeachdell' usually bears clusters of flowers of peach coloration, whereas 'CHEwarvel' bears flowers of medium yellow coloration with less clusters. The new variety is classified as a shrub with a very upright to nearly columnar growth habit, whereas the seed parent is classified as a climbing miniature with a more spreading growth habit.

The new variety may be distinguished from its pollen parent, 'DICmagic' by the following combination of characteristics: whereas 'CHEwpeachdell' bears double (about 26 to 32 petals and about 22 to 30 petaloids) flowers of peach coloration, 'DICmagic' bears flowers of orange and yellow coloration with significantly less petalage and petaloides. The new variety is classified as a shrub with a very upright to nearly columnar tall growth habit, whereas the pollen parent is classified has a miniature with a more compact and significantly shorter growth habit.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of September. Phenotypic expression may vary with environmental, cultural and climatic conditions, as well as differences in conditions of light and soil.

FLOWER

The new variety sometimes bears its flowers singly, usually in clusters of two to five or more per stem. Flowers may be borne in regular rounded to somewhat flat clusters on strong somewhat short to medium length stems (about 28 to about 75 cm.). Outdoors, the plant blooms abundantly and nearly continuously during the growing season. The flowers have a slight tea fragrance.

BUD

The peduncle is about 1.2 to about 3.6 cm. in length, of somewhat slender to average caliper (about 0.15 to about 0.3 cm. in diameter), and usually erect. It is moderately smooth, with some stipitate glands, and some hairs. Peduncle color is between 144A and 148A sometimes very lightly suffused, especially on the side exposed to the sun, with near 183C.

Before the calyx breaks, the bud is about 0.8 to about 1.3 cm. in diameter at the widest point, about 1.5 to about 2.3 cm. in length, and pointed to moderately ovoid in shape. The surface of the bud bears some moderately long slender foliaceous appendages and few stipitate glands, usually with slender entire foliaceous parts extending beyond the tip of the bud about ¼ or more of its length. Bud color is between 144A and 147B sometimes lightly suffused, especially on the side exposed to the sun, with between 187B and 183B.

The sepals are about 1.7 to about 2.1 cm. in length and about 0.6 to about 0.8 cm. in width at the widest point. The outer surface color of the sepal is between 144A and 147B sometimes lightly suffused, especially on the side exposed to the sun, with between 187B and 183B. The inner surface color of the sepal is between 138B and 137C and covered with fine wooly tomentum; sepal margins are lined with few stipitate glands and hairs.

As the petals open (after the calyx breaks), the bud is about 1.4 to about 1.9 cm. in diameter at the widest point, about 1.6 to about 2.1 cm. in length, and moderately flat-topped to globular in form. The color of the under and upper surfaces of the newly opened petals is between 28B and 26D. At the point where the petal attaches on the upper surfaces, there is a moderately small zone of between 14B and 13B. At the point where the petal attaches on the under surfaces, there is a small zone of near 13C.

BLOOM

When fully open, the bloom ranges from about 4.4 to about 5.6 cm. in diameter. The flower receptacle size is about 0.7 to about 1 cm. Petalage is double with about 26 to 32 petals and about 22 to 30 petaloids irregularly arranged. When partially open, the bloom form is moderately cupped to globular, and the petals are moderately tightly spiraled to cupped with petal edges somewhat reflexed outward. When fully open, the bloom form is less cupped, and the petals are more loosely to slightly cupped with petal edges somewhat reflexed outward.

PETALS

The substance of the petals is moderately heavy and of medium thickness, with upper surfaces moderately shiny to slightly satiny and under surfaces matte to somewhat shiny. The outer petals are nearly obovate to somewhat oval in shape with usually mucronate to sometimes rounded apices. The inner petals are nearly obovate to somewhat oblanceolate in shape with usually mucronate to sometimes rounded apices. The petals are about 1.5 to about 2.4 cm. in length and about 0.7 to about 2.1 cm. in width at the widest point. Petal margins are entire.

NEWLY OPENED FLOWER

The under surface color of the outer, intermediate and inner petals is between 28C and 29C. At the point where the petal attaches, there is a moderately small large zone of between 12B and 13C.

The upper surface color of the outer, intermediate and inner petals is between 28B and 29B. At the point where the petal attaches, there is a moderately small zone of near 12B.

The general tonality of the newly opened flower is between 28B and 29B.

The flower contains about 22 to 30 petaloids irregularly arranged. The substance of the petaloids is moderately heavy and of medium thickness, with upper surfaces moderately shiny to slightly satiny and under surfaces matte to somewhat shiny. The petaloids are nearly obovate to somewhat oblanceolate in shape with usually mucronate to sometimes rounded apices. The under surface color of the petaloids is between 28C and 29C. At the point where the petaloids attaches, there is a moderately small zone of between 12B and 13C. The upper surface color of the petaloids is between 28B and 29B. At the point where the petaloids attaches, there is a moderately small zone of near 12B. The petaloids are about 0.5 to about 1.2 cm. in length and about 0.3 to about 0.6 cm. in width at the widest point. Petaloids margins are entire.

THREE-DAY-OLD FLOWER

The under surface color of the outer and inner petals is between 38D and 36C. At the point where the petal attaches, there is a moderately large zone of between 12D.

The upper surface color of the outer and inner petals is between 38C and 20D. At the point where the petal attaches, there is a moderately large zone of between 8C and 10C.

The general tonality of the three-day-old flower is between 38C and 20D.

On the spent bloom, the petals usually drop off cleanly.

In September in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens vary in number (average about 61) and are arranged regularly about the pistils; many are mixed with petaloids. The filaments are of medium length (about 0.6 to about 0.9 cm.), most with anthers. Filaments are between 13A and 14B in color. The anthers are somewhat small for the class and all open approximately at the same time. Anther color is between 22A and 26A when immature and between 164C and 165A at maturity. Pollen is abundant.

FEMALE REPRODUCTIVE ORGANS

Pistils vary in number (average about 69). The styles are moderately even, somewhat short in length (about 0.2 to about 0.5 cm.), thin in caliper, and moderately loosely bunched. Stigma color is between 11C and 13D. Style color is between 53A and 60A. Ovaries are usually all enclosed in the calyx.

Hips are of average length (about 1.7 to about 2.1 cm.), flat at the top and somewhat globular to urn-shaped in form, and between 30B and 30C in color when ripe. The hip surface is very smooth with thick fleshy walls. The sepals are permanent. The seeds are irregularly rounded, smooth in texture, approximately 4 to about 8 per hip, about 0.3 to about 0.5 cm. in diameter at the widest point and between 164D and 163C in color.

FOLIAGE

The compound leaves are usually comprised of three to seven or more leaflets and are borne abundantly. The seven-leaflet leaves are about 7.8 to about 9.4 cm. in length and about 4.2 to about 5.8 cm. in width at the widest point, moderately leathery to somewhat crisp in texture, and semi-glossy finish. The terminal leaflets are about 2.1 to about 3.6 cm. in length and about 1.3 to about 2.0 cm. in width at the widest point, shaped narrowly oval to somewhat broadly lanceolate with mostly acute to slightly acuminate apices and rounded bases. Their margins are usually simply serrate.

The upper surface color of the mature leaf is between 147A and 137B. The under surface color of the mature leaf is between 147B and 138B. The upper surface color of the young leaf is between 146A and 144A, sometimes moderately suffused especially toward the very edge of the leaves with between 187C and 183C. The under surface color of the young leaf is between 146B and 138B, sometimes moderately suffused with between 187C and 183C.

The rachis is light in caliper and moderately rough. The upper side is nearly flat to very shallowly grooved with many hairs and very few stipitate glands on the edges of the grooves. The under side of the rachis is moderately rough with some hairs and stipitate glands and a few small prickles. The rachis color is between 146C and 146B, moderately suffused on the young leaf with between 187C and 183C.

The stipules are about 0.9 to about 1.3 cm. in length and of medium width (about 0.3 to about 0.5 cm.) with moderately short to medium straight points that usually turn out at an angle of more than 45 degrees and sometimes slightly recurve toward the stem. The stipules color is between 146C and 146B, moderately suffused on the young leaf with between 187C and 183C.

The petiole is about 0.4 to about 1.0 cm. in length and about 0.1 to about 0.15 cm in diameter at the widest point. The petiole color is between 146C and 146B.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a very upright to almost columnar tall growing habit (about 175 to about 250 cm. in height and about 88 to about 125 cm. spread at the widest point), with very full branching. It displays very vigorous growth and the canes are of somewhat light to medium caliper.

The color of the major stems is between 146C and 146D. They bear many large prickles that are about 0.5 to about 1.0 cm. in length. The large prickles are almost straight to angled slightly downward with a very long moderately narrow oval base; prickle color is between 166B and 166C. The major stem bears few small prickles of similar shape and coloration.

The color of the branches is between 146B and 147B. They bear many large prickles which are of similar size and shape to the large prickles on the major stems; prickle color is between 162C and 160B sometimes lightly suffuses near the base with near 182C. The branches bear few small prickles of similar shape and coloration.

The color of the new shoots is between 144A and 148A sometimes moderately suffused especially on the side facing the sun with between 187C and 183C. They bear some large prickles which are of similar size and shape to the large prickles on the major stems. The shoots bear very few small prickles of similar shape and coloration. Prickle color is between 187C and 185C.

I claim:

1. A new and distinct Shrub rose plant of the variety substantially as described and illustrated herein.

* * * * *

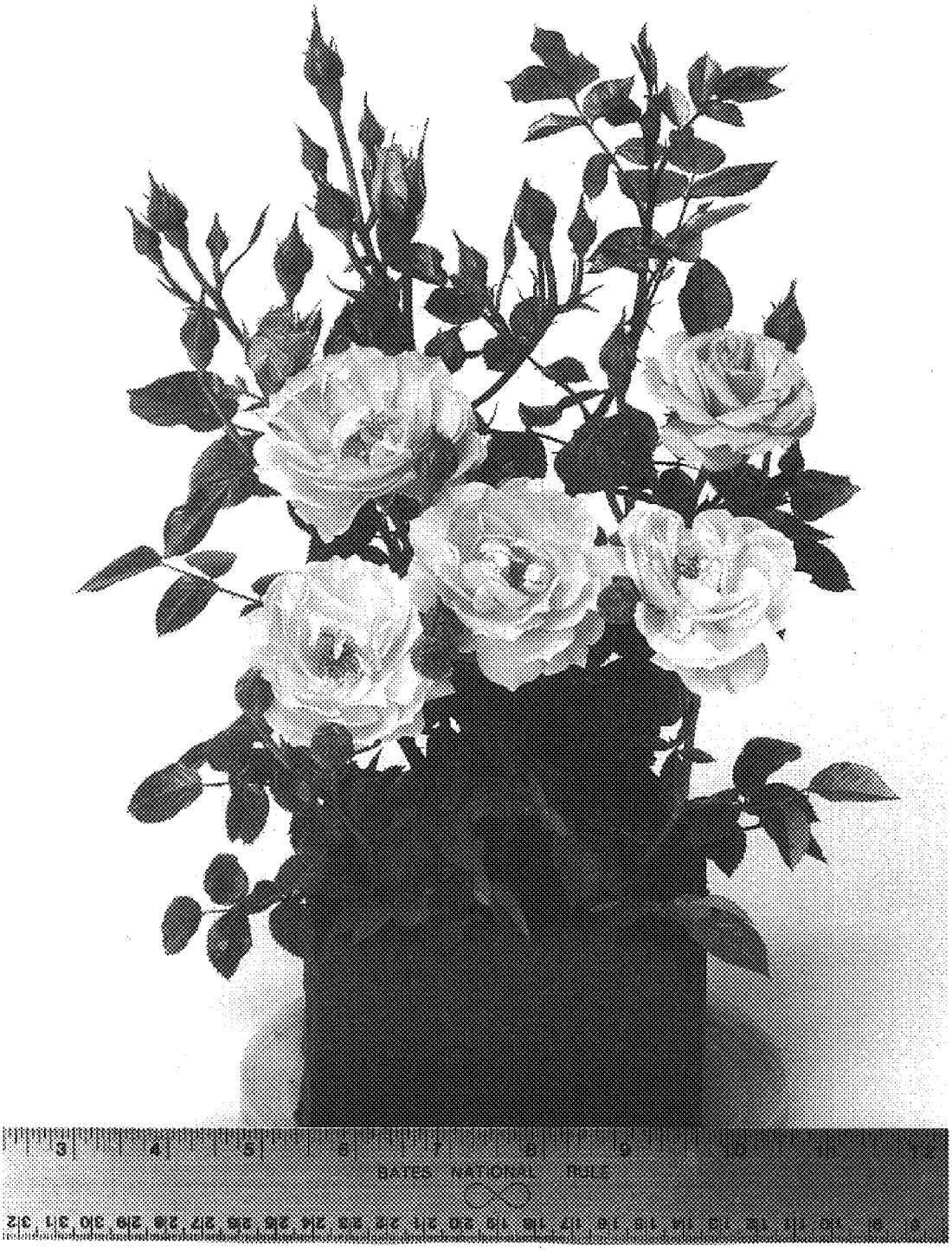
GATES NATIONAL RULE